United States Patent [19]
Sansom et al.

[11] Patent Number: 5,197,962
[45] Date of Patent: Mar. 30, 1993

[54] COMPOSITE ELECTROSURGICAL MEDICAL INSTRUMENT

[75] Inventors: Matthias R. Sansom, Sandy; Richard L. Ellingson, Draper, both of Utah

[73] Assignee: MegaDyne Medical Products, Inc., Murray, Utah

[21] Appl. No.: 918,936

[22] Filed: Jul. 22, 1992

Related U.S. Application Data

[63] Continuation of Ser. No. 711,618, Jun. 5, 1991, abandoned.

[51] Int. Cl.[5] ............................................. A61B 17/35
[52] U.S. Cl. ................................. 606/45; 606/49; 606/29
[58] Field of Search ............................ 606/27–29, 606/37–52; 427/329

[56] References Cited

U.S. PATENT DOCUMENTS

| | | | |
|---|---|---|---|
| 4,161,950 | 7/1979 | Doss et al. | 606/50 |
| 4,302,374 | 11/1981 | Helle et al. | 260/29.6 F |
| 4,314,559 | 2/1982 | Allen | 606/45 |
| 4,333,467 | 6/1982 | Domicone | 606/49 |
| 4,862,890 | 9/1989 | Stasz et al. | 606/48 |
| 4,868,066 | 9/1989 | Whitmore | 428/551 |
| 4,981,756 | 1/1991 | Rhandhawa | 428/336 |
| 5,030,218 | 7/1991 | Alexander | 606/45 |

Primary Examiner—Peter A. Aschenbrenner

[57] ABSTRACT

An electrosurgical instrument for causing hemostasis having a first predetermined region for contact with flesh or tissue, said instrument being coated over at least a portion of said predetermined region by a composite coating consisting essentially of a nickel-phosphorous matrix having particles of polytetrafluoroethylene distributed substantially uniformly therein.

6 Claims, 1 Drawing Sheet

COMPOSITE ELECTROSURGICAL MEDICAL INSTRUMENT

This application is a continuation, of application Ser. No. 07/711,618 filed Jun. 5, 1991, abandoned.

DESCRIPTION OF THE PRIOR ART

This invention relates to medical instruments, and more particularly to those which are adapted for use in circumstances in which an electrical current is passed through the instrument.

Electrically activated instruments are known in the art, such as coagulation forceps, suction cautery devices, and electrode cautery tips, the last noted including ball-tip, needle, extended and flat blade electrodes. These various types of medical instruments are employed in procedures that involve cutting and/or other contact with flesh or exposed tissue. Thus, for example, surgical blade electrodes are utilized to cut through tissue, and such cutting often results in substantial bleeding. Such bleeding may interfere with successful completion of the procedure and should be controlled or terminated. Accordingly, electrical current is utilized to cauterize the exposed tissue. For this purpose, the blade electrodes are affixed to handpieces which have means can be activated for passing electrical energy into the blade to cause it to transmit radio-frequency electrical energy therefrom to the flesh or tissue and cauterize. The same is true for the other electrosurgical devices noted above. However, in the process of cauterization, the problem of sticking of charred or otherwise cauterized tissue and blood to the medical implement has arisen. Such sticking is troublesome and even where not threatening the success of the procedure, is annoying and time-consuming requiring frequent cleaning of the medical instrument.

Various proposals have heretofore been advanced for solving the problem of tissue sticking on such electrosurgical devices. Thus, for example, various coatings have been proposed for adherence to these medical instruments so as to render the surfaces less adherent, but none are entirely satisfactory. These include among others, (1) coating the entire working surface with a non-stick plastic (2) coating a part of the working surface with a non-stick plastic and (3) applying a non-stick plastic coating which includes islands of metallic material or metallic material embedded therein to assist in electrical conductivity. Coating the entire surface with a very thin coating is most satisfactory in terms of non-adherence, but as resulted in dulling cutting edges, coating only a part has resulted in charring and sticking on the uncoated part; and applying coatings with islands of metal in non-stick material has nonetheless resulted in excessive charring and sticking. Moreover, some such coatings have involved complex production procedures and unsatisfactory performance. There is also the problem with some non-stick plastic coating of flaking-off to some extent which can be deleterious to the person or animal being treated.

The proposals of the prior art in some instances have brought an improvement in reducing the amount of charring of tissue and adherence to electrosurgical instruments. However, it has been necessary to coat essentially the entire surface that somes in contact with the flesh or tissue and the like or not exceed a low level of metallic islands in order to achieve an acceptable level of charring and adherence. Moreover, the addition of a coating which completely eliminates metallic contact with tissue resulted in some undesired dulling of these electrosurgical instruments which are alos used for cutting.

Although, according to some prior proposals, most, but not all, of an electrosurgical blade was covered, leaving but a minor portion exposed at an edge, this has brought about sticking and charring of tissue at the edge, obviously an undesirable result. Accordingly, there has been a continuing need for further improvements in medical instrument coatings.

BRIEF DESCRIPTION OF THE PRESENT INVENTION

In contrast with the proposals of the prior art, it has been discovered that, contrary to expectation, a coating can be applied which presents a majority surface area of metal and a minority of surface areas, or islands, of non-stick material and which nevertheless exhibits excellent non-stick characteristics.

This is accomplished through the utilization of a particular form of an electroless nickel/phosphorous plating solution coupled with a predetermined mixture of polytetrafluoroethlyene material, whereby the entire intended working area on an electrosurgical instrument may be coated while retaining desired electrical conductivity, sharpness of cutting edge and elimination of tissue sticking, and avoiding any flaking of the non-stick material from the instrument during use.

A mixture of electroless nickel/phosphorus is mixed with a lesser quantity of polytetrafluoroethylene to provide a composite solution that coats the exposed surface of an electrosurgical medical instrument, thereby imparting to it the above described superior cutting, conducting and non-sticking characteristic.

OBJECTS AND FEATURES OF THE PRESENT INVENTION

It is one general object of the invention to improve coated electrosurgical medical instruments.

It is another object of this invention to simiplify appliation of suitable coatings to electrosurgical medical instruments.

It is yet another object of the invention to improve the characteristics of coated electrosurgical medical instruments.

Accordingly, in accordance with one feature of the invention, a composite electroless nickel/phosphorus polytetrafluoroethylene coating is applied to at least selected portions of the exterior working surface of the electrosurgical medical instrument, thereby simplifying application.

In accordance with another feature of the invention, the coating is principally metallic, thereby providing excellent conduction of retention of sharpness of cutting surface, yet simultaneously providing excellent non-sticking characteristics.

These and other objects and features of the invention will be apparent from the following detailed description.

DETAILED DESCRIPTION OF THE INVENTION

While the invention is applicable to any electrosurgical instrument that comes into contact with flesh, tissue, and the like, such as the coagulation forceps, suction cautery devices, and electrode cautery tips discussed above, it will be particularly described in connection with blade electrodes which are used for cutting and coagulation (cauterizing). Also, as used herein the term "working surface" means the portion of the instrument meant to come into contact with the flesh, tissue, and the like.

Figure 1:
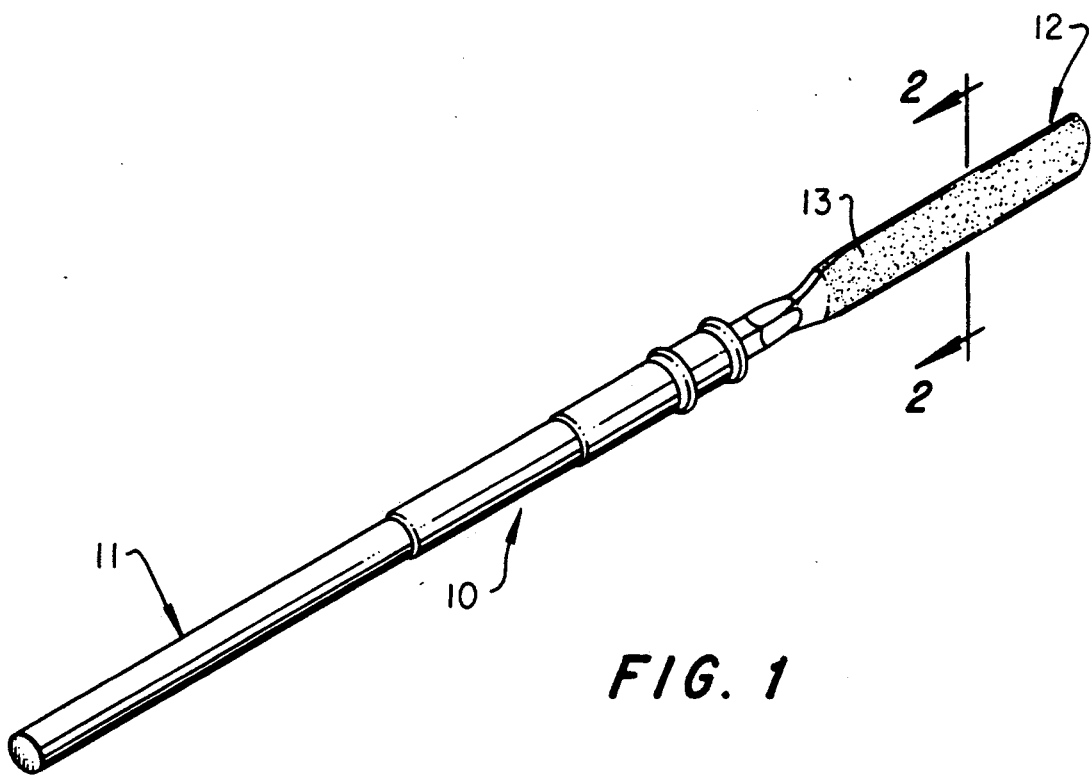
FIG. 1 is a perspective view of an electrosurgical blade electrode which has been coated in accordance with the principles of the invention.

Now turning to the drawings and more particularly to FIG. 1 thereof, it will be observed that there is therein disclosed an electrosurgical flat blade electrode 10 having a proximal end 11 for insertion into a handle and working surface 12. The exterior of working surface 12 has coating 13 thereon. Not shown is the conventional handle, usually referred to as an electrosurgical pencil into which the blade is inserted for use, which handle has means enabling electric current to flow to the blade to permit cauterizing when desired by the user.

As known to those skilled in the art, in such blades, the characteristic of cleanliness (freedom from adherent tissue) is hightly essential. Moreover, it is important to the successful use of the electrosurgical blades that the blade remain clean and that it not be impeded by the adherence of any substance (such as blood, tissue, and the like) which may stick to the blade when it is in the coagulation (cauterizing) mode as this may retard or interfere with its use either to cauterize or to cut.

Surgical implements such as that depicted in FIG. 1 are typically formed of stainless steel or other similar non-corrosive materials. Although the principles of the invention are applicable to such blades and other electrosurgical implements made of such material, it has been found that the instruments may be of other substances such as, for example, brass, nickel, aluminum, other types of steel, or alloys. The principles of the invention may also be employed with non-metallic conductive substances provided that they possess the inherent qualities of stability and integrity sufficient to meet the desired requisites; i.e. certain conductive plastics.

The key aspect of the invention is the coating applied to at least the working surface of the electrosurgical instrument. It must be a composite coating of a nickel/-phosphorous alloy matrix having particles of polytetrafluoroethylene (PTFE) substantially uniformily distributed therethrough.

The thickness of the coating is not critical; it is only necessary that the coating be of a thickness sufficient to provide the desired non-stick characteristics without impeding the desired electrical characteristics. Ordinarily, a thickness of about 0.1 to 0.5 mil is suitable, with a thickness of 0.2 mil being optimum.

As to the nickel-phosphorous alloy used to form the matrix it can be any that can be plated into a surface by conventional electroless or autocatalytic plating; i.e., a plating that relies on chemical rather than electrical energy. Preferred alloys are those containing about 2 to 14 wt. % phosphorous.

As to the PTFE it can be any PTFE particles, preferably of sub-micron size, used to form non-stick coatings. Particularly suitable are those that are suitable for plating as set forth in U.S. Pat. No. 4,302,374.

As to proportions, the major component of the composite is the nickel-phosphorous alloy with the PTFE used in minor amounts, usually less than 30% by volume and usually from about 18 to 25% by volume of the composite.

Such nickel-phosphorous alloy and PTFE compositions are commercially available under the trade name "Niflor" sold by Fothergill & Harvey PLC, of Long Causeway, Leeds, England LS9 ONY and also generally available through commercial sources in the United States. Examples of such commercial sources are Lincoln Plating Company of 600 West E Street, Lincoln, Nebr. 68522 and the Enthone Corporation of West Haven, Conn. Such Niflor PTFE dispersions consist essentially of conventional electroless nickel-phosphorus in a plating solution solution to which there have been added less than about 25% by weight PTFE and selected surfactants (as described in U.S. Pat. No. 4,302,374) which enable the polytetrafluorethylene polymer to be co-deposited as particles in a nickel-phosphorous matrix as the plating proceeds. The solution is carefully selected to ensure that no toxic materials are in the final coating. The typical bath material by weight, is about 85% nickel, 7% phosphorus and 8% PTFE.

The process of coating the working surface does not form a part of the instant invention, but is that conventionally used to coat a surface using the NIFLOR PTFE dispersions discussed above. This electroless process results in coatings having a substantially uniform thickness with the nickel-phosphorous matrix having particles of PTFE distributed substantially uniformly therethrough so that some PTFE is on the exposed outer surface of the coating.

Figure 2:
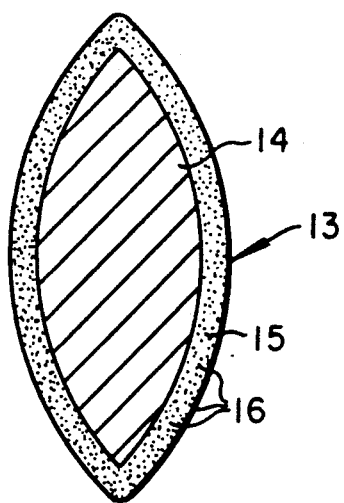
FIG. 2 is a section view along line 2—2 of FIG. 1.

This is best illustrated in FIG. 2 which shows underlying blade substrate 14 with coating 13 consisting of a nickel-phosphorous matrix 15 having particles of PTFE 16 distributed therethrough as well as some at the surface of coating 13. It is preferred to coat the entire portion of the blade which is to come into contact with the flesh or tissue, although in some instances an edge of the blade or some other portion thereof that may, but does not ordinarily come into contact with the flesh or tissue may be left uncoated.

A typical deposited coating will contain about 84.6% by weight nickel, 7.0% by weight phosphorous, and 8.4% by weight PTFE (which corresponds 25% by volume). The coating has a density of about 6.5 g/ml and a hardness, as deposited, of about 300 VHN.

It will now be evident that there has been described herein an improved medical instrument. Although the inventive concepts hereof have been illustrated by way of a preferred embodiment, it will be evident to those skilled in the art that other adaptions and modifications may be employed without departing from the sprit and the scope of the inventions.

This is particularly true with respect to coagulation forceps since the instant coating can be placed on the flesh or tissue portions of the tips without baking of forceps which is required for plastic coatings such a Teflon. Such baking will destroy or adversely affect the electrical elements thereof. With the electroless containing no such heating is required.

The terms and expressions used herein are employed as terms of description and not of limitation; and consequently, there is no intent in the use thereof of excluding any and all equivalents, but on the contrary, it is intended to include all adaptations and modifications that may be employed without departing from the spirit and scope of the invention as defined in the claims.

What is claimed is:

1. An electrosurgical instrument to which electric current can be applied for causing hemostasis, having an electrically conductive predetermined region for contact with flesh or tissue, said instrument being coated over at least a portion of said predetermined region by a composite coating consisting essentially of a nickel-phosphorous matrix having particles of polytetrafluoroethylene distributed substantially uniformly therethrough.

2. The electrosurgical instrument of claim 2 wherein said entire predetermined region is coated with said composite coating.

3. The electrosurgical instrument of claim 2 wherein said instrument is an electrosurgical blade electrode.

4. The electrosurgical instrument of claim 3 wherein the thickness of said coating is about 0.1 to 0.5 mil.

5. The electrosurgical instrument of claim 2 wherein said instrument is a coagulation forceps.

6. The electrosurgical instrument of claim 5 wherein the thickness of said coating is about 0.1 to 0.5 mil.

* * * * *